United States Patent [19]
Stampa et al.

[11] Patent Number: 6,084,100
[45] Date of Patent: Jul. 4, 2000

[54] PROCESS FOR THE PREPARATION OF LORATADINE

[75] Inventors: Alberto Stampa; Pelayo Camps, both of Barcelona; Gloria Rodriguez; Jordi Bosch, both of Girona; Maria del Carmen Onrubia, Barcelona, all of Spain

[73] Assignee: Medichem, S.A., Barcelona, Spain

[21] Appl. No.: 09/058,837

[22] Filed: Apr. 13, 1998

Related U.S. Application Data

[60] Provisional application No. 60/048,083, May 30, 1997.
[51] Int. Cl.[7] .................................. C07D 221/06
[52] U.S. Cl. ............................................. 546/93
[58] Field of Search ................................. 546/93

*Primary Examiner*—Dwayne C. Jones
*Attorney, Agent, or Firm*—Scully, Scott, Murphy & Presser

[57] ABSTRACT

The process consists of the reductive coupling between the compounds: 8-chloro-5,6-dihydrobenzo[5,6]cyclohepta[1,2-b]pyridin-11-one (formula VII)

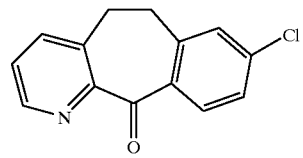

and ethyl 4-oxopiperidine-1-carboxylate (formula IV)

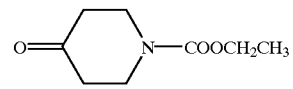

through the action of low-valent titanium species.

13 Claims, No Drawings

PROCESS FOR THE PREPARATION OF LORATADINE

This application claims benefit from U.S. Provisional Application Ser. No. 60/048,083, filed on May 30, 1997.

FIELD OF THE INVENTION

The present invention concerns to a process for the preparation of loratadine, based on the cross reductive coupling between 8-chloro-5,6-dihydrobenzo[5,6]cyclohepta[1,2-b]pyridin-11-one and ethyl 4-oxopiperidine-1-carboxylate.

PRIOR ART

Loratadine is a known antihistaminic disclosed for the first time by F. J. Villani in the U.S. Pat. No. 4,282,233.

preparation of intermediate II, which require the use of superacids and Grignard reagents.

Process (B) from scheme 1, disclosed in the ES patent 2.040.177, implies the use of trimethyl phosphite, whose manipulation from an industrial viewpoint is inconvenient.

Process (C) from scheme 1, disclosed in the ES patents 2.009.465 and 2.009.466, is, in practice, a simple variation of process (A) in which the order of their two last reactions has been interchanged.

Finally, process (D) was disclosed in the ES patent 2.080.700 and in the Canada patent 2.134.128, while the preparation of intermediate VI, also disclosed in the ES patent 2.080.699, was carried out through a multy-step and complex process.

According to the previous knowledge, it remains the need for the development of processes: a) shorter, b) involving reaction conditions easy to be carried out industrially, for

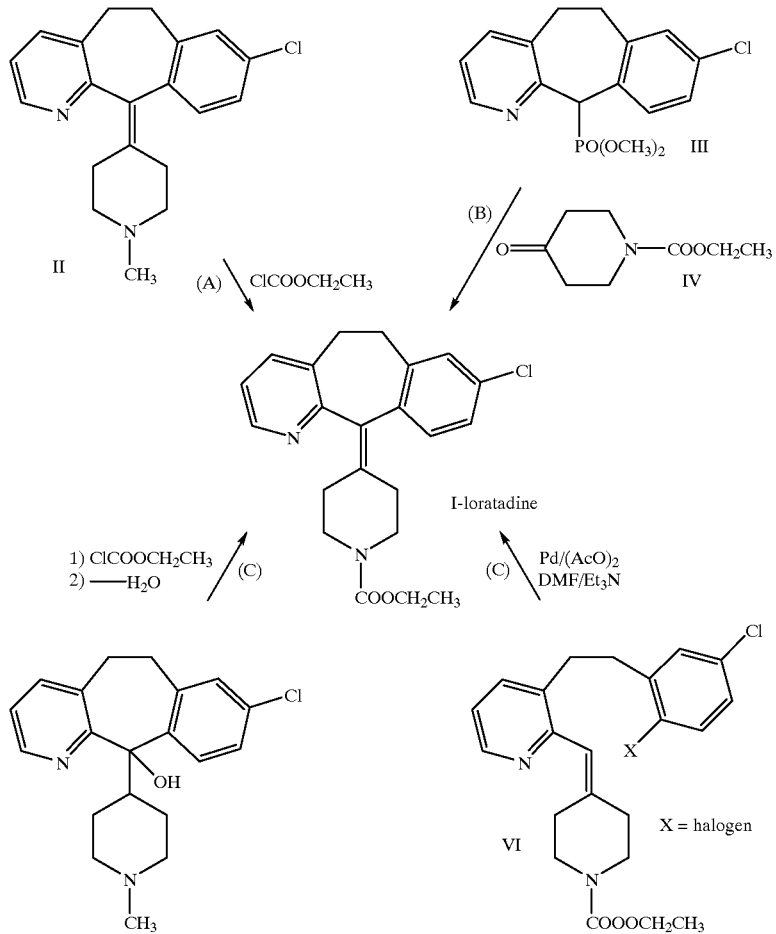

Scheme 1

Several alternative processes for the preparation of loratadine are known, which can be summarized through the reactions shown in Scheme 1.

Process (A) from scheme 1 was disclosed in the above cited U.S. Pat. No. 4,282,233 and in the ES patent 503.085, while the required intermediate II, can be obtained through a multi-step cumbersome process disclosed in the U.S. Pat. No. 3,326,924, which requires the use of Grignard reagents. The U.S. Pat. Nos. 4,659,716, 4,731,447 and 4,873,335 disclose complex and multi-step alternative processes for the instance, not requiring the use of superacids or Grignard reagents, c) not involving the use of unstable reagents, such as 4-chloro-N-methylpiperidine, or of inconvenient manipulation from an industrial viewpoint, such as trimethyl phosphite.

OBJECT OF THE INVENTION

The object of the present invention is a process for the preparation of loratadine, based on the use of easily available starting compounds and reaction conditions easily to apply in an industrial process.

DESCRIPTION OF THE INVENTION

The process for the preparation of loratadine of the present invention is characterized by reacting, in an organic solvent and in the presence of a tertiary amine, 8-chloro-5,6-dihydrobenzo[5,6]cyclohepta[1,2-b]pyridin-11-one (formula VII)

VII

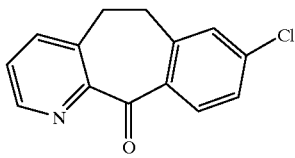

and ethyl 4-oxopiperidine-1-carboxylate (formula IV)

IV

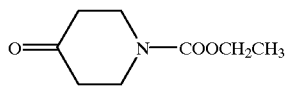

with low-valent titanium species.

The conversion of the starting compounds, VII and IV, into loratadine, I, takes place by reductive cross coupling, based on the reaction known as the McMurry reaction.

Many papers on the McMurry reaction have been published, as can be seen from the revision published by J. E. McMurry in Chem. Rev., 89, 1513–1524 (1989).

Most of the described reactions consist in the dimerization of a carbonyl compound and, although there are know cross couplings between two different carbonyl compounds, most of them are intramolecular reactions. In an intermolecular cross coupling reaction between two carbonyl compounds, three kind of products can be formed: two corresponding to the dimerization of each carbonyl component and one corresponding to the cross coupling. A priori, a statistic distribution of these products, which could be modified by using an excess of one of the carbonyl components, is to be expected. In any case, the result would be the formation of a mixture of products, whose separation might be difficult.

Consequently, it was not foreseeable to the expert that the reductive coupling of 8-chloro-5,6-dihydrobenzo[5,6]cyclohepta[1,2-b]pyridin-11-one, VII, and ethyl 4-oxopiperidine-1-carboxylate, IV, induced by low-valent titanium species could be adequate for the industrial preparation of loratadine.

Compound VII, 8-chloro-5,6-dihydrobenzo[5,6]cyclohepta[1,2-b]pyridin-11-one, can be easily obtained according to the U.S. Pat. No. 3,326,924 or to ES patent 554.898.

Compound IV, ethyl 4-oxopiperidine-1-carboxylate, is an easily available compound, cited and disclosed in many scientific references, for instance in the ES patent 2.040.177.

The reducing low-valent titanium species may be generated by reduction of titanium trichloride with lithium aluminum hydride, potassium, magnesium, or by reduction of titanium tetrachloride with zinc, among other procedures. However, from an industrial viewpoint, the use of titanium tetrachloride in combination with zinc dust is highly preferred, since titanium trichloride is very expensive and is unstable vs the air oxygen and the humidity.

Any inert organic solvent, i.e.: a solvent neither able to react with the starting compounds nor with the reactive species, preferably an ethereal solvent such as diethyl ether, 1,4-dioxane, 1,2-dimethoxyethane, tetrahydrofuran, etc., can be used.

The tertiary amines are well-known by the expert and among them, for instance, triethylamine, ethyldiisopropylamine, tributylamine and pyridine, can be cited.

A preferred but not limitative sequence of operations to carry out the process of the present invention can be as follows:

a) the low-valent titanium species are prepared by reduction of titanium tetrachloride with zinc dust in an appropriate solvent.

b) a tertiary amine is added.

c) a mixture of ketones VII and IV is added, and the mixture is heated for the required time to complete the reaction, and d) loratadine is isolated from the reaction mixture.

In this preferred but not limitative sequence of operations, the reaction can be performed as shown below.

In an adequate reaction vessel, the reaction solvent is charged (usually, diethyl ether, 1,4-dioxane, 1,2-dimethoxyethane, tetrahydrofuran, etc.) and the solvent is cooled to a temperature comprised between 10 and −20° C. Then, titanium tetrachloride is slowly added (1 to 4 mol per mol VII) and zinc dust (2 to 8 mol per mol VII) keeping at any time the temperature of the reaction mixture between the above indicated values. Then, a specific amount of a tertiary amine (pyridine, triethylamine, etc., 1 to 3 mol per mol VII) and finally, a solution of VII and IV (1 to 2 mol per mol of VII) in the same solvent used before are added, keeping the temperature in the above cited range. The mixture thus obtained is stirred at room temperature for several hours and then it is heated to a temperature comprised between 30° C. and the reflux temperature of the solvent, for 6 to 72 hours. When the reaction is completed, loratadine is isolated from the reaction mixture by conventional procedures and purified by crystallization in an appropriate solvent.

The process of this invention show advantages vs the previously disclosed processes since, giving rise to the product in an acceptable yield, reduces the number of synthetic operations avoiding the use of corrosive (superacids) or unstable reagents (4-chloro-N-methylpiperidine) or of inconvenient manipulation from an industrial viewpoint (trimethyl phosphite).

An example of the application of this process, which should be considered as illustrative and not limitative of the scope of the present invention, is described below.

EXAMPLE 1

Preparation of Loratadine

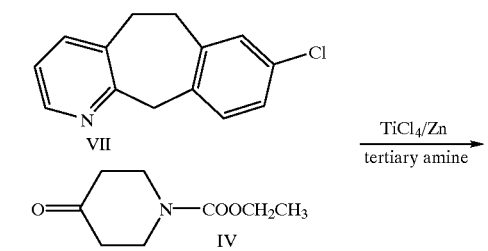

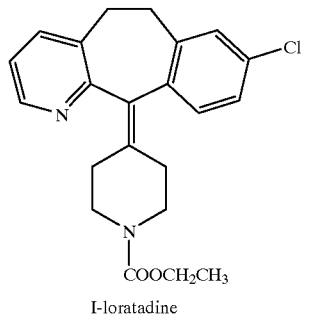

I-loratadine

In a two-liter vessel provided with a thermometer, a reflux condenser and nitrogen atmosphere, dry tetrahydrofuran (343 ml) was placed, and cooled between 0 and −5° C. Titanium tetrachloride (28.5 ml, 49.5 g, 0.255 mol) was slowly added with stirring (17 min.), keeping the temperature in the above indicated range, a yellow suspension being formed. After the addition was finished, stirring was continued for 10 min. Then, zinc dust (34.5 g, 0.524 mol) was added with stirring in approximately 15 min. keeping the temperature in the above cited range, and after addition was finished, stirring was continued at this temperature for 20 min., a blue suspension being formed. Then, pyridine (17 ml, 0.21 mol) was added with stirring, keeping the temperature in the above range, and then, a solution of 8-cholro-5, 6-dihydrobenzo[5,6]cyclohepta[1,2-b]pyridin-11-one, VII, (30.0 g, 0.123 mol) and ethyl 4-oxopiperidine-1-carboxylate, IV, (25.2 g, 0.147 mol) in anhydrous tetrahydrofuran (96 ml) was added in about 20 min., with stirring and keeping the temperature in the above cited range. The, thus obtained, dark brown mixture was stirred for 3 h keeping the temperature in the above cited range, then was allowed to heat to room temperature and kept at this temperature for 2 h and then heated to 40° C. for 17 h, keeping the stirring all over this period of time.

The tetrahydrofuran was distilled off from the reaction mixture to give a black resin that was dissolved in dichloromethane (300 ml) and acidified by addition of isopropanol/HCl 7.2 N (97 ml). The mixture was stirred for 10 min, and the phases were separated, being the aqueous one extracted with dichloromethane (150 ml). The combined organic phases were washed 6 times with a mixture of water (125 ml) and 35% aqueous HCl (7.5 ml). Then, the organic phase was basified to pH 7.5–8.0 by addition of 30% aqueous NH$_3$. The mixture was stirred for 10 min. and the phases were separated, and then washed 3 times with water (250 ml). The organic phase was dried with anhydrous sodium sulfate, filtered and the solvent eliminated in vacuo to give a residue (47.47 g) that was treated with acetonitrile (97 ml). The, thus formed, solid was filtered and crystallized from the same solvent to give pure loratadine, m.p. 132–133° C. (18.8 g, 40% yield).

What we claim is:

1. A process for the preparation of loratadine consisting of reacting, in an organic solvent and in the presence of a tertiary amine, 8-chloro-5,6-dihyrobenzo[5,6]cyclohepta[1,2-b]pyridin-11-one, of formula VII

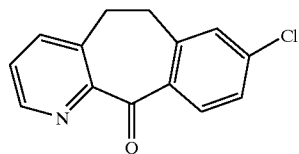

and ethyl 4-oxopiperidine-1-carboxylate of formula IV

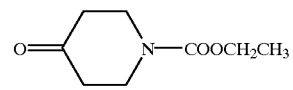

with low-valent titanium species.

2. The process of claim 1, wherein the low-valent titanium species are generated by reduction of titanium tetrachloride with zinc dust.

3. The process of claim 2, wherein the preparation of the low-valent titanium species is carried out at a temperature comprised between 10 and −20° C.

4. The process of claim 3, wherein the preparation of the low-valent titanium species is carried out at a temperature comprised between 0 and −5° C.

5. The process of claim 1, wherein the organic solvent used is an ether.

6. The process of claim 5, wherein such ether is diethyl ether, tetrahydrofuran, 1,2-dimethoxyethane, 1,4-dioxane.

7. The process of claim 1, wherein the tertiary amine is triethylamine, ethyldiisopropylamine, tributylamine, or pyridine.

8. The process of claim 7, wherein the tertiary amine is pyridine.

9. The process of claim 1, wherein the reaction of the compound of formula VII and the compound of formula IV is carried out at a temperature comprised between 30° C. and the reflux temperature of the used solvent.

10. The process of claim 9, wherein the reaction is carried out at a temperature comprised between 30 and 50° C.

11. The process of claim 1, wherein the reaction time for the reaction of the compound of formula VII and the compound of formula IV is comprised between 4 and 72 hours.

12. The process of claim 11, wherein the reaction time is comprised between 6 and 24 hours.

13. A process to obtain loratadine consisting of the steps of:
   a) preparing low-valent titanium species by reduction of titanium tetrachloride with zinc dust in an organic solvent,
   b) adding a tertiary amine,
   c) adding a mixture of 8-chloro-5,6-dihydrobenzo[5,6]-cyclohepta[1,2-b]pyridin-11-one and ethyl 4-oxopiperidine-1-carboxylate and heating the reaction mixture for the required time to complete the reaction, and
   d) isolating loratadine from the reaction mixture.

* * * * *